(12) United States Patent
Hoffmann et al.

(10) Patent No.: US 7,160,881 B2
(45) Date of Patent: Jan. 9, 2007

(54) CRYSTALLINE MODIFICATIONS OF 2-(3,5-BIS-TRIFLUOROMETHYL-PHENYL)-N-[6-(1,1-DIOXO-1 $\lambda^6$-THIOMORPHOLIN-4-YL)-4-(4-FLUORO-2-METHYL-PHENYL)-PYRIDIN-3-YL]-N-METHYL-ISOBUTYRAMIDE

(75) Inventors: Torsten Hoffmann, Weil am Rhein (DE); Fabienne Hoffmann-Emery, Weil am Rhein (DE); Sonja Nick, Basel (CH); Urs Schwitter, Reinach (CH); Pius Waldmeier, Wegenstetten (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 34 days.

(21) Appl. No.: 10/766,122

(22) Filed: Jan. 27, 2004

(65) Prior Publication Data

US 2004/0186100 A1    Sep. 23, 2004

(30) Foreign Application Priority Data

Jan. 31, 2003    (EP)    ................... 03002134

(51) Int. Cl.
 *C07D 279/10* (2006.01)
 *C07D 279/12* (2006.01)
 *C07D 295/00* (2006.01)
 *A61K 31/54* (2006.01)
(52) U.S. Cl. .................. 514/227.5; 544/58.2
(58) Field of Classification Search ............... 544/58.2; 514/227.8, 227.5
 See application file for complete search history.

(56) References Cited

U.S. PATENT DOCUMENTS 5,972,938 A    10/1999    Rupniak et al.
2003/0004157 A1    1/2003    Buser et al.

FOREIGN PATENT DOCUMENTS

| EP | 1 035 115 A1 | 9/2000 |
|---|---|---|
| GB | 2347422 | 9/2002 |
| WO | WO 95/16679 | 6/1995 |
| WO | WO 95/18124 | 7/1995 |
| WO | WO 95/23798 | 9/1995 |
| WO | WO 02/085458 | 10/2002 |

OTHER PUBLICATIONS

Navari, et al., *New England J. of Medicine*, vol. 340, pp. 190-195 (1999).
Maggi et al., *J. Auton. Pharmacol.*, vol. 13, pp. 23-93 (1993).
Kramer et al., *Science*, vol. 281, pp. 1640-1645 (1998).
Longmore et al., *Can. J. Physiol. Pharmacol.*, vol. 75, pp. 612-621 (1997).
Barker, *Reviews in Neurosciences*, vol. 7, pp. 187-214 (1996).
Quartara et al., *Neuropeptides.*, vol. 32(1), pp. 1-49 (1998).
Doi et al., *Eur. J. of Pharmacology.*, vol. 383(3), pp. 297-303 (1999).
Palma et al., *Life Sciences.*, vol. 67(9), pp. 985-1001 (2000).
Mutra et al., *Nature.*, vol. 405, pp. 180-183 (2000).
Stout et al., Neurokinin 1 Receptor Antagonists as Potential Antidepressants, *Annu. Rev. Pharmacol. Toxicol.* vol. 41, pp. 877-906 (2001).
Rupniak, N., Elucidating the antidepressant actions of substance P ($NK_1$ receptor) antagonists, *Current Opinion in Investigational Drugs*, vol. 3(2), pp. 257-261 (2002).
Humphrey, J., Medicinal Chemistry of Selective Neurokinin-1 Antagonists, *Current Topics in Medicinal Chemistry*, vol. 3, pp. 1423-1435 (2003).

*Primary Examiner*—Kahsay Habte
(74) *Attorney, Agent, or Firm*—George W. Johnston; Patricia S. Rocha-Tramaloni; Kimberly J. Prior

(57) ABSTRACT

The present invention relates to a new crystalline modification of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide characterized by the following X-ray diffraction pattern obtained with a $Cu_{K\alpha}$, radiation at 2θ (2Theta)=4.5, 6.4, 7.5, 7.7, 8.0, 8.2, 10.0, 10.2, 10.9, 11.1, 12.9, 13.4, 14.0, 14.5, 15.1, 15.6, 16.2, 16.5, 17.3, 17.5, 18.0, 18.9, 19.3, 19.5, 19.9, 20.1, 20.6, 21.0, 21.4, 22.7, 23.1 and 23.6 and an infrared spectrum having sharp bands at 2925, 2854, 1637, 1604, 1484, 1395, 1375, 1285, 1230, 1172, 1125, 1082, 999, 943, 893, 868, 860, 782, 705, 684 $cm^{-1}$, and wherein the extrapolated melting point (DSC) is 137.2° C.

6 Claims, 8 Drawing Sheets

CRYSTALLINE MODIFICATIONS OF 2-(3,5-BIS-TRIFLUOROMETHYL-PHENYL)-N-[6-(1,1-DIOXO-1λ⁶-THIOMORPHOLIN-4-YL)-4-(4-FLUORO-2-METHYL-PHENYL)-PYRIDIN-3-YL]-N-METHYL-ISOBUTYRAMIDE

FIELD OF THE INVENTION

The present invention relates to a novel crystalline form of 2-(3,5-bis-trifluoromethyl-phenyl)-N-[6-(1,1-dioxo-1λ⁶-thiomorpholin-4-yl)-4-(4-fluoro-2-methyl-phenyl)-pyridin-3-yl]-N-methyl-isobutyramide (modification A), methods for producing this novel crystalline form, and its use in pharmaceutical formulations.

BACKGROUND OF THE INVENTION 2-(3,5-bis-Trifluoromethyl-phenyl)-N-[6-(1,1-dioxo-1λ⁶-thiomorpholin-4-yl)-4-(4-thiomorpholin-4-yl)-4-(4-fluoro-2-methyl-phenyl)-pyridin-3-yl]-N-methyl-isobutyramide in its modification B is known and described in PCT/EP02/083 11.

2-(3,5-bis-Trifluoromethyl-phenyl)-N-[6-(1,1-dioxo-1λ⁶-thiomorpholin-4-yl)-4-(4-fluoro-2-methyl-phenyl)-pyridin-3-yl]-N-methyl-isobutyramide has been described as active on the NK1 receptor for the treatment of diseases, related to this receptor, such as migraine, rheumatoid arthritis, asthma, bronchial hyperreactivity, inflammatory bowel disease or for the treatment of disorders including Parkinson's disease, anxiety, depression, pain, headache, Alzheimer's disease, multiple sclerosis, oedema, allergic rhinitis, Crohn's disease, ocular injury, ocular inflammatory diseases, psychosis, motion sickness, induced vomiting, emesis, urinary incontinence, psychoimmunologic or psychosomatic disorders, cancer, withdrawal symptoms of addictive drugs from opiates or nicotine, traumatic brain injury or benign prostatic hyperplasia.

SUMMARY OF THE INVENTION

The present invention relates to a novel crystalline form of

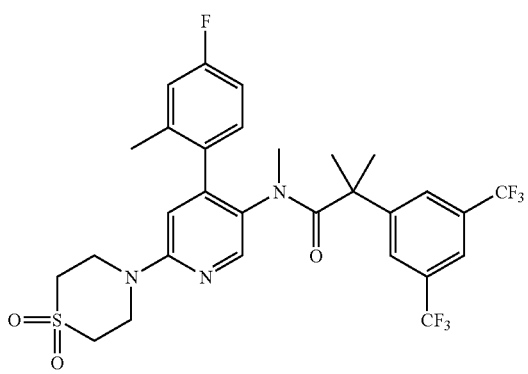

2-(3,5-bis-trifluoromethyl-phenyl)-N-[6-(1,1-dioxo-1λ⁶-thiomorpholin-4-yl)-4-(4-fluoro-2-methyl-phenyl)-pyridin-3-yl]-N-methyl-isobutyramide (modification A).

It has been found that 2-(3,5-bis-trifluoromethyl-phenyl)-N-[6-(1,1-dioxo-1λ⁶-thiomorpholin-4-yl)-4-(4-fluoro-2-methyl-phenyl)-pyridin-3-yl]-N-methyl-isobutyramide can be isolated, depending upon the method of preparation, in 3 different crystalline modifications (A, B and C) and in amorphous form which are distinguishable by their infra-red spectra, X-ray powder diffraction patterns and their melting behaviour.

It also has been found that the A modification of the above mentioned compound has an improved pharmaceutical profile, especially in the case of oral administration. The compound can be formulated at high concentrations in a composition further comprising certain selected adjuvants. Such formulations have a better substance resorption and thus an improved bioavailability compared with formulations which contain 2-(3,5-bis-trifluoromethyl-phenyl)-N-[6-(1,1-dioxo-1λ⁶-thiomorpholin-4-yl)-4-(4-fluoro-2-methyl-phenyl)-pyridin-3-yl]-N-methyl-isobutyramide in its B or C modification.

Amorphous material has also an improved bioavailability in a microsuspension form, but this form is not suitable for oral administration in humans.

Thus, the present invention provides pharmaceutical compositions containing a the A modification, or a pharmaceutically acceptable salt thereof, and a pharmaceutically acceptable carrier.

In accordance with the invention, modification A as well as pharmaceutically acceptable salts of modification A are useful in the control or prevention of illnesses based on the NK1 receptor. Such illnesses include migraine, rheumatoid arthritis, asthma, bronchial hyperreactivity, inflammatory bowel disease. The invention also provides for the treatment of illnesses based on the NK1 receptor, such as Parkinson's disease, anxiety, depression, pain, headache, Alzheimer's disease, multiple sclerosis, oedema, allergic rhinitis, Crohn's disease, ocular injury, ocular inflammatory diseases, psychosis, motion sickness, induced vomiting, emesis, urinary incontinence, psychoimmunologic or psychosomatic disorders, cancer, withdrawal symptoms of addictive drugs from opiates or nicotine, traumatic brain injury, and benign prostatic hyperplasia.

DETAILED DESCRIPTION OF THE INVENTION

Figure 1:
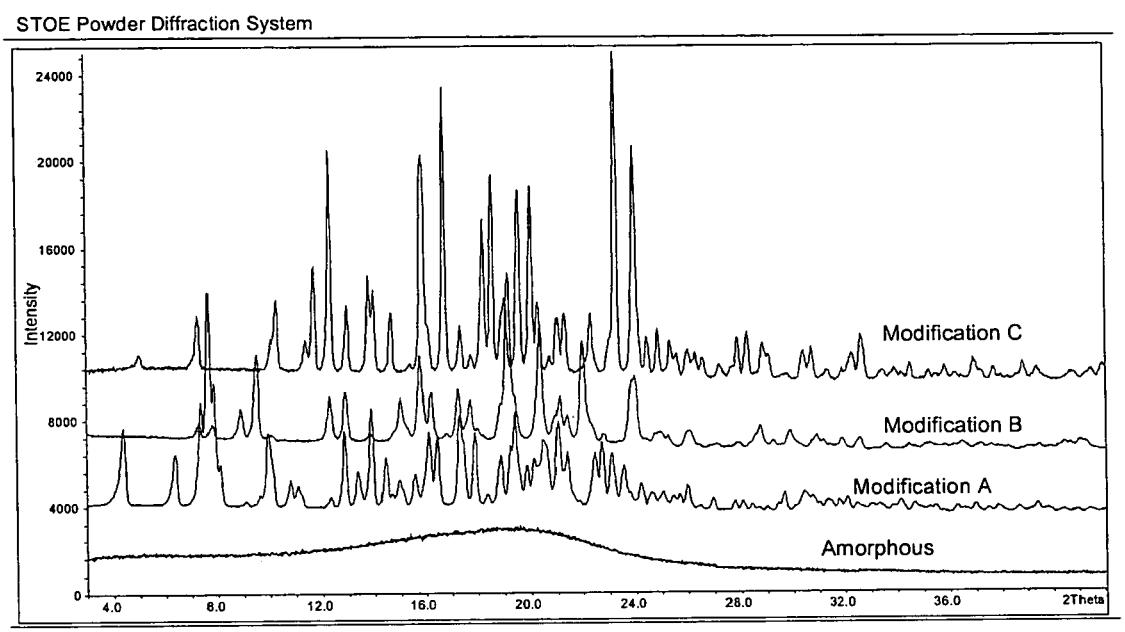
FIG. 1: XRPD patterns of typical lots of different crystal modifications and amorphous state of 2-(3,5-bis-trifluoromethyl-phenyl)-N-[6-(1,1-dioxo-1λ⁶-thiomorpholin-4-yl)-4-(4-fluoro-2-methyl-phenyl)-pyridin-3-yl]-N-methyl-isobutyramide.

The present invention relates to a novel crystalline form of

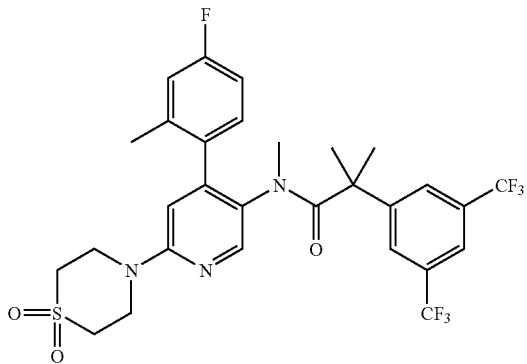

2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide (modification A).

It has been found that 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide can be isolated, depending upon the method of preparation, in 3 different crystalline modifications (A, B and C) and in amorphous form which are distinguishable by their infra-red spectra, X-ray powder diffraction patterns and their melting behaviour.

It also has been found that the A modification of the above mentioned compound has an improved pharmaceutical profile, especially in the case of oral administration. The compound can be formulated at high concentrations in a composition further comprising certain selected adjuvants. Such formulations have a better substance resorption and thus an improved bioavailability compared with formulations which contain 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide in its B or C modification.

Amorphous material has also an improved bioavailability in an micro-suspension form, but this form is not suitable for oral administration in human.

2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide in its modification B may be prepared in accordance with PCT/EO02/083 11. Modifications A, B and C or amorphous form of 2-(3,5-bis-Trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide can be prepared via the new higher yielding route as described below:

Scheme

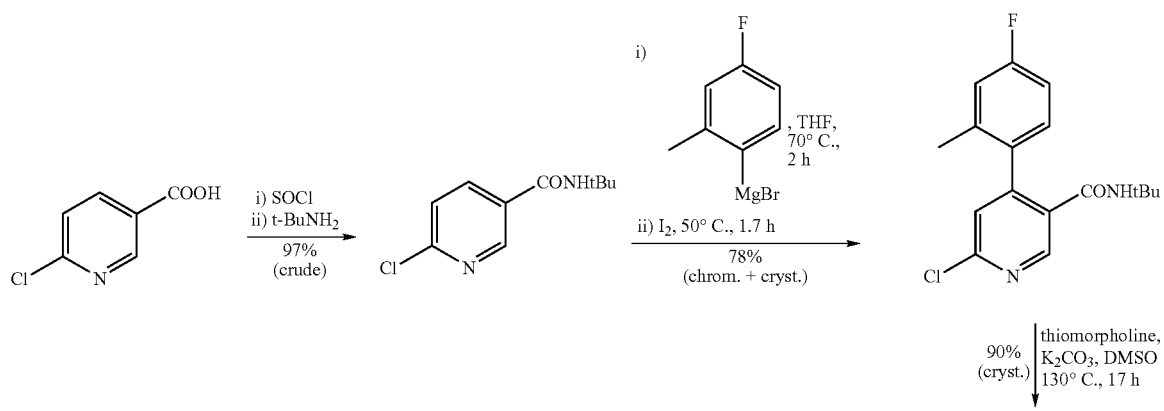

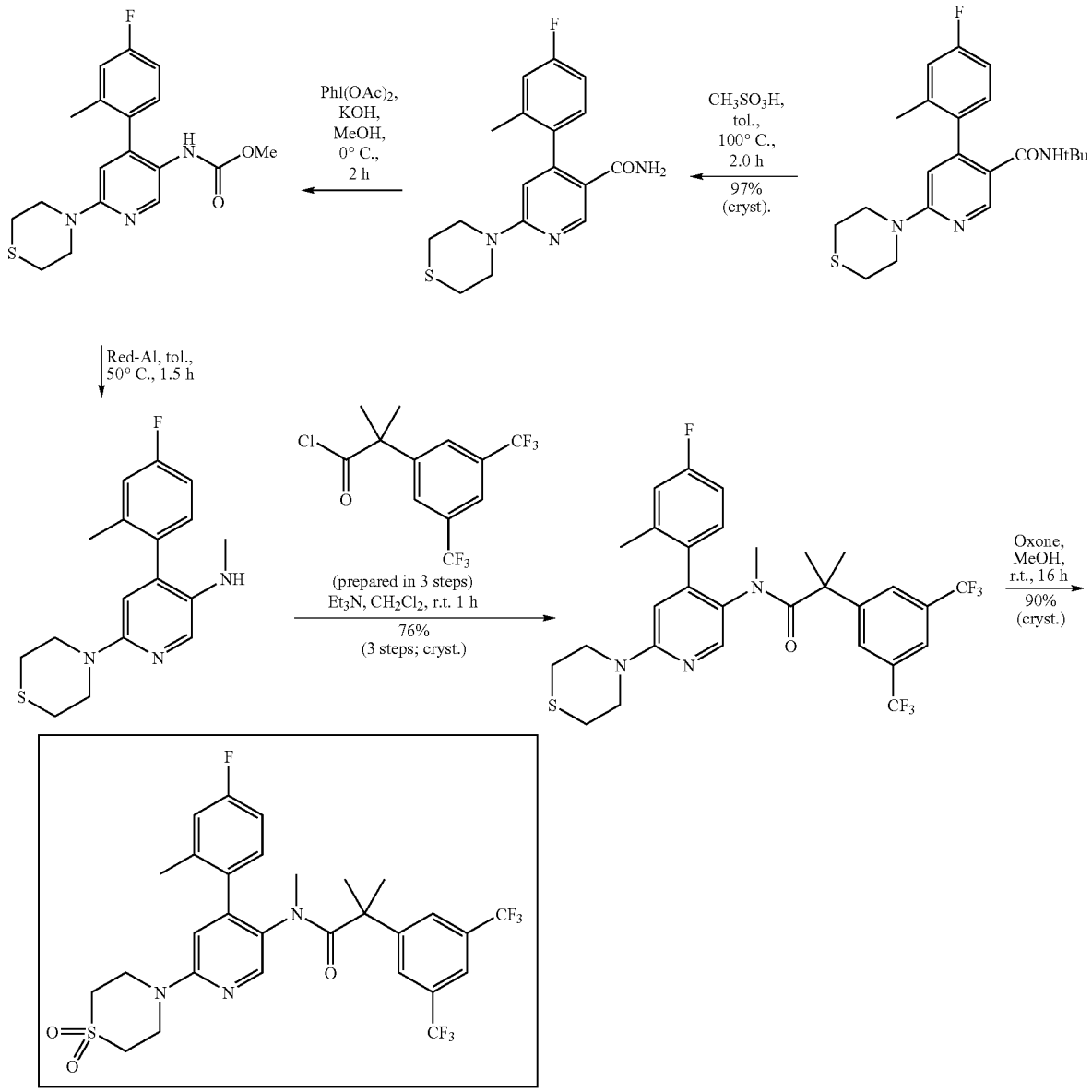

In general, N-tert-Butyl-6-chloro-4-(4-fluoro-2-methyl-phenyl)-nicotinamide can be prepared by suspending magnesium under argon in tetrahydrofurane. The suspension is then treated under reflux with a solution of 2-bromo-5-fluorotoluene in tetrahydrofurane. After the addition of the first 3 ml of this solution, the mixture is warmed to start a Grignard reaction. The reaction mixture is stirred under reflux, cooled, and added within about 10 minutes to a solution of N-tert-butyl-6-chloronicotinamide in tetrahydrofurane (exothermic reaction). The mixture is then stirred and cooled to room temperature. A solution of iodine in tetrahydrofurane is slowly added to the reaction mixture (exothermic reaction). The resulting suspension is stirred, treated with water at room temperature, poured onto 2 N aqueous sulfuric acid, and treated with tert-butyl-methyl-ether. After vigorous stirring, the phases are separated and the organic phase washed with half-saturated aqueous sodium bicarbonate and with half-saturated aqueous sodium chloride. The aqueous phases are then extracted with tert-butyl-methyl-ether. The combined organic extracts are dried, concentrated in a rotary evaporator, and dried under high vacuum at room temperature to produce a yellow oil. This oil is dissolved in dichloromethane and filtered through silica gel, eluting with hexane and then with dichloromethane. The fractions with the product are collected and concentrated under reduced pressure, followed by addition of hexane. The solution is concentrated in a rotary evaporator followed by treatment with hexane under stirring. The precipitate is filtered off, washed with cold hexane:ethyl acetate 19:1(−20° C.) and dried under high vacuum to yield N-tert-butyl-6-chloro-4-(4-fluoro-2-methyl-phenyl)-nicotinamide as a light beige powder. The mother liquors are then concentrated in a rotary evaporator providing an orange solid, which can be purified by chromatography on silica gel, eluting with hexane and then with hexane:ethyl acetate 9:1. The fractions with the product are collected, concentrated, and dried under high vacuum to yield N-tert-butyl-6-chloro-4-(4-fluoro-2-methyl-phenyl)-nicotinamide as a light beige powder.

N-tert-Butyl-4-(4-fluoro-2-methyl-phenyl)-6-thiomorpholin-4-yl-nicotinamide can be then produced by dissolving N-tert-Butyl-6-chloro-4-(4-fluoro-2-methyl-phenyl)-nicotinamide in dimethylsulfoxide and potassium carbonate, followed by the addition of thiomorpholine. The resulting suspension is stirred, cooled to room temperature, and partitioned between ethyl acetate and half-saturated aqueous sodium chloride solution. The phases are then separated and the organic phase washed with half-saturated aqueous sodium chloride. The aqueous phases are then extracted with ethyl acetate. The combined organic extracts are dried and concentrated in a rotary evaporator to produce a yellow oil. This oil is heated with the dropwise addition of n-hexane to obtain a refluxing suspension, which can be cooled to room temperature and further stirred at 0° C. for about one hour. The precipitate is filtered off, washed with cold n-hexane:ethyl acetate 9:1, and dried in a vacuum oven to yield N-tert-butyl-4-(4-fluoro-2-methyl-phenyl)-6-thiomorpholin-4-yl-nicotinamide as a light beige powder.

4-(4-Fluoro-2-methyl-phenyl)-6-thiomorpholin-4-yl-nicotinamide can be produced by suspending N-tert-Butyl-4-(4-fluoro-2-methyl-phenyl)-6-thiomorpholin-4-yl-nicotinamide in toluene. The suspension is heated with the dropwise addition of methanesulfonic acid to provide an emulsion, which is then stirred and cooled to room temperature. The phases are separated and the organic phase washed with deionized water. The combined aqueous phases are cooled to about 0° C., followed by the slow addition of 28% aqueous sodium hydroxide to increase the pH to about 12.5. The suspension obtained then can be extracted with dichloromethane. The combined organic extracts are dried and concentrated in a rotary evaporator. Propyl acetate is then added, and the solution concentrated in a rotary evaporator. A second portion of propyl acetate is added, and the solution concentrated to form a suspension. N-hexane is added to the suspension, followed by stirring. The resulting precipitate is filtered off, washed with n-hexane:propyl acetate 9:1, and dried in a vacuum oven to yield 4-(4-fluoro-2-methyl-phenyl)-6-thiomorpholin-4-yl-nicotinamide as a light yellow powder.

[4-(4-Fluoro-2-methyl-phenyl)-6-thiomorpholin-4-yl-pyridin-3-yl]-carbamic acid methyl ester can be produced by adding 4-(4-Fluoro-2-methyl-phenyl)-6-thiomorpholin-4-yl-nicotinamide to a solution of potassium hydroxide in methanol and cooling to a temperature of about 0° C. Methanol is then added, followed by the addition in one portion of (diacetoxyiodo)benzene (exothermic). The reaction is allowed to proceed at about 0° C., and then the reaction mixture is allowed to warm to room temperature, followed by dilution with deionized water and concentration in a rotary evaporator. The residue is diluted with ethyl acetate, the phases separated, and the aqueous phase further extracted with ethyl acetate. The organic phases are washed with half-saturated aqueous sodium chloride. The combined organic extracts are dried, concentrated under reduced pressure, and dried under high vacuum to yield [4-(4-fluoro-2-methyl-phenyl)-6-thiomorpholin-4-yl-pyridin-3-yl]-carbamic acid methyl ester as a brown sticky oil which can be used in the next step without purification.

Methyl-[4-(4-fluoro-2-methyl-phenyl)-6-thiomorpholin-4-yl-pyridin-3-yl]-amine can be produced by diluting Red-Al in toluene and adding this solution dropwise to a solution of [4-(4-fluoro-2-methyl-phenyl)-6-thiomorpholin-4-yl-pyridin-3-yl]-carbamic acid methyl ester in toluene. The yellow solution obtained is stirred at room temperature, cooled to about 0° C., and poured slowly onto a mixture of 4 N aqueous sodium hydroxide and ice (very exothermic). After stirring, the phases are separated, the aqueous phase extracted with tert-butyl-methyl-ether, and the organic phases washed with brine. The combined organic extracts are dried and concentrated under reduced pressure to yield methyl-[4-(4-fluoro-2-methyl-phenyl)-6-thiomorpholin-4-yl-pyridin-3-yl]-amine as a brown oil which can be used in the next step without further purification.

2-(3,5-Bis-trifluoromethyl-phenyl)-N-methyl-N-[4-(4-fluoro-2-methyl-phenyl)-6-thiomorpholin-4-yl-pyridin-3-yl]-isobutyramide is produced by adding a solution of 2-(3,5-bis-trifluoromethyl-phenyl)-2-methyl-propionyl chloride in dichloromethane dropwise at room temperature to a solution of methyl-[4-(4-fluoro-2-methyl-phenyl)-6-thiomorpholin-4-yl-pyridin-3-yl]-amine and triethylamine in dichloromethane. The reaction mixture is stirred for about 1 hour and poured onto 1 N aqueous sodium hydroxide. After extraction, the phases are separated, the aqueous phase extracted with dichloromethane, and the organic phases washed with water. The combined organic extracts are concentrated under reduced pressure, and the solvent is exchanged for ethanol. The solution is seeded with some crystals, water slowly added, and the system stirred at room temperature and then at about 0° C. The precipitate is filtered off, washed with cold ethanol (0° C.) and dried under high vacuum to yield 2-(3,5-bis-trifluoromethyl-phenyl)-N-methyl-N-[4-(4-fluoro-2-methyl-phenyl)-6-thiomorpholin-4-yl-pyridin-3 -yl]-isobutyramide as an off-white powder.

2-(3,5-Bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide can be produced by suspending 2-(3,5-Bis-trifluoromethyl-phenyl)-N-methyl-N-[4-(4-fluoro-2-methyl-phenyl)-6-thiomorpholin-4-yl-pyridin-3-yl]-isobutyramide in methanol and treating it at room temperature with oxone™ (potassium peroxymonosulfate). The suspension is then stirred for about 16 hours at room temperature and cooled to about 0° C., followed by the dropwise addition of sodium hydrogen sulfite solution. After stirring at room temperature, the pH is adjusted to about 8.5 with saturated aqueous sodium carbonate. The methanol is then evaporated under reduced pressure, and the residue is extracted with dichloromethane. The organic phase is washed with half-saturated aqueous sodium chloride. The solvent is exchanged under reduced pressure in a rotary evaporator with isopropanol, and the volume reduced. The solution is cooled to room temperature under stirring and stirred further for about 1 hour. The precipitate formed is filtered off, washed with isopropanol, and dried under high vacuum to yield 2-(3,5-bis-trifluoromethyl-phenyl)-N-[6-(1,1-dioxothiomorpholin-4-yl)-4-(4-fluoro-2-methyl-phenyl)-pyridin-3-yl]-N-methyl-isobutyramide as a white powder.

The different modifications A, B and C and the amorphous form can be prepared from 2-(3,5-bis-trifluoromethyl-phenyl)-N-[6-(1,1-dioxothiomorpholin-4-yl)-4-(4-fluoro-2-methyl-phenyl)-pyridin-3-yl]-N-methyl-isobutyramide as follows:

Modification A can be prepared by dissolving 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide in 2-propanol at reflux conditions. After polishing filtration, the solution is stirred and linearly cooled to about 10° C. over a period of about 6 h. The slurry is stirred for an additional period at about 10° C., followed by harvesting of the crystals by filtration. The colorless solid is rinsed with cold 2-propanol (10° C.) and dried in vacuum (5 mbar) to produce 2-(3,5-bis-trifluoromethyl-phenyl)-N-[6-

(1,1-dioxothiomorpholin-4-yl)-4-(4-fluoro-2-methyl-phenyl)-pyridin-3-yl]-N-methyl-isobutyramide in crystal modification A.

Crystal modification A also can be prepared using 1-propanol instead of 2-propanol, but otherwise following the protocol above. Alternatively, crystal modification A is obtained from any other modification known by digestion with 1-propanol, 2-propanol or a mixture of ethanol/dichloromethane/water.

Modification B can be prepared by dissolving 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide ethanol. After polishing filtration, the solution is stirred and linearly cooled to about 20° C. over a period of about 48 h. After filtration, the colorless solid is rinsed with ethanol and dried in vacuum (5 mbar), yielding 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide in crystal modification B.

Alternatively, crystal modification B is obtained by digestion of any other modification known with acetonitrile, cyclohexane, ethanol, n-hexane, methanol, methyl t-butyl ether or water.

Modification C can be prepared by incubating 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide in modification A at about 120° C. in vacuum (5 mbar) for a period of about 3 days. 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide in crystal modification C is obtained after cooling to ambient temperature.

Amorphous 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide can be prepared in the following manner. A solution of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide in dichloromethane is rapidly vacuum concentrated at room temperature using a rotary evaporator. The resulting slightly beige foam is further dried in vacuum (5 mbar) at ambient temperature for a period of about 12 h, yielding 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide in amorphous state.

Alternatively, amorphous material is obtained by fast evaporation of solutions in dioxane, ethyl acetate, isopropyl acetate, methyl ethyl ketone or tetrahydrofurane.

The crystal modifications and the amorphous material may clearly be distinguished by their physicochemical data as described below.

XRPD (X-Ray Powder Diffraction)

XRPD patterns were recorded for each of modifications A, B, and C and amorphous 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide on a Bruker D8 diffractometer in reflexion mode as described in Example 12. The results, depicted in FIG. 1, show that the crystal modifications A, B and C and the amorphous material can clearly be distinguished by their X-ray powder diffraction patterns.

Infrared Spectroscopy (IR)

Figure 2:
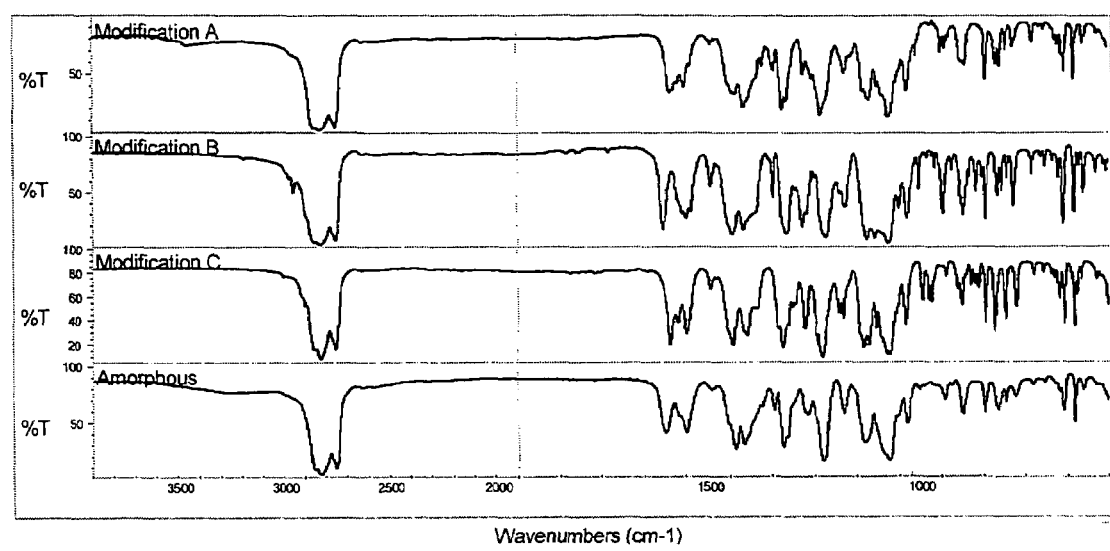
FIG. 2: IR spectra of typical lots of different crystal modifications and amorphous state of 2-(3,5-bis-trifluoromethyl-phenyl)-N-[6-(1,1-dioxo-1λ⁶-thiomorpholin-4-yl)-4-(4-fluoro-2-methyl-phenyl)-pyridin-3-yl]-N-methyl-isobutyramide.
Figure 3:
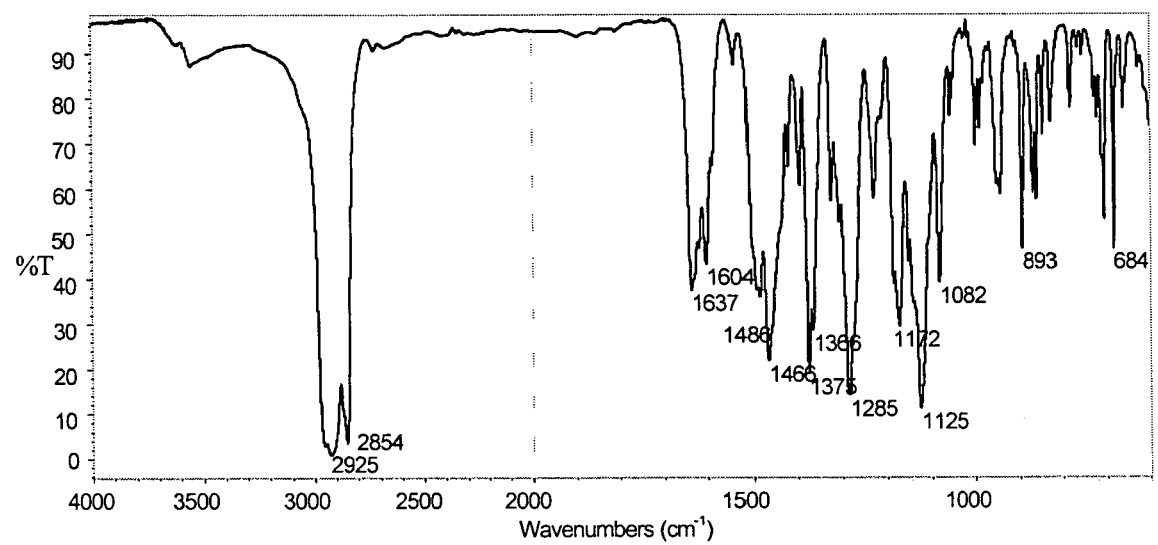
FIG. 3: IR spectra of modification A, IR bands: 2925, 2854, 1637, 1604, 1484, 1395, 1375, 1285, 1230, 1172, 1125, 1082, 999, 943, 893, 868, 860, 782, 705, 684 cm⁻¹.

The IR-spectra of modifications A, B, and C and amorphous 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide are recorded as film of a Nujol suspension as described in Example 13. The crystal modifications A, B, C and amorphous state can also clearly be distinguished by solid state IR as shown in FIGS. 2 and 3.

Differential Scanning Calorimetry (DSC)

Figure 4:
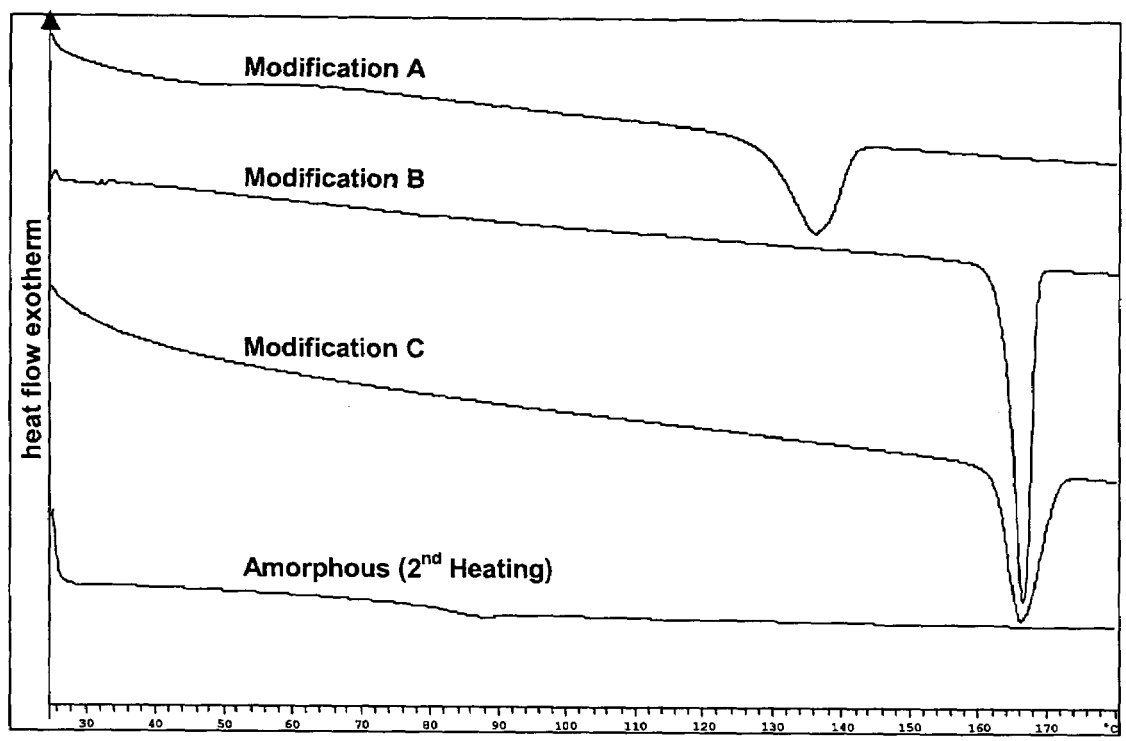
FIG. 4: DSC thermograms of typical lots of different crystal modifications and amorphous state of 2-(3,5-bis-trifluoromethyl-phenyl)-N-[6-(1,1-dioxo-1λ⁶-thiomorpholin-4-yl)-4-(4-fluoro-2-methyl-phenyl)-pyridin-3-yl]-N-methyl-isobutyramide.

The DSC-thermograms for each of modifications A, B, and C and amorphous 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide were recorded using a Mettler-Toledo differential scanning calorimeter as described in Example 14. The crystal modifications A, B and C can be distinguished by their melting behavior as depicted in FIG. 4 and Table 1. As also shown in FIG. 4 and Table 1, amorphous material exhibits a glass transition.

Dynamic Vapor Sorption (DVS)

Figure 5:
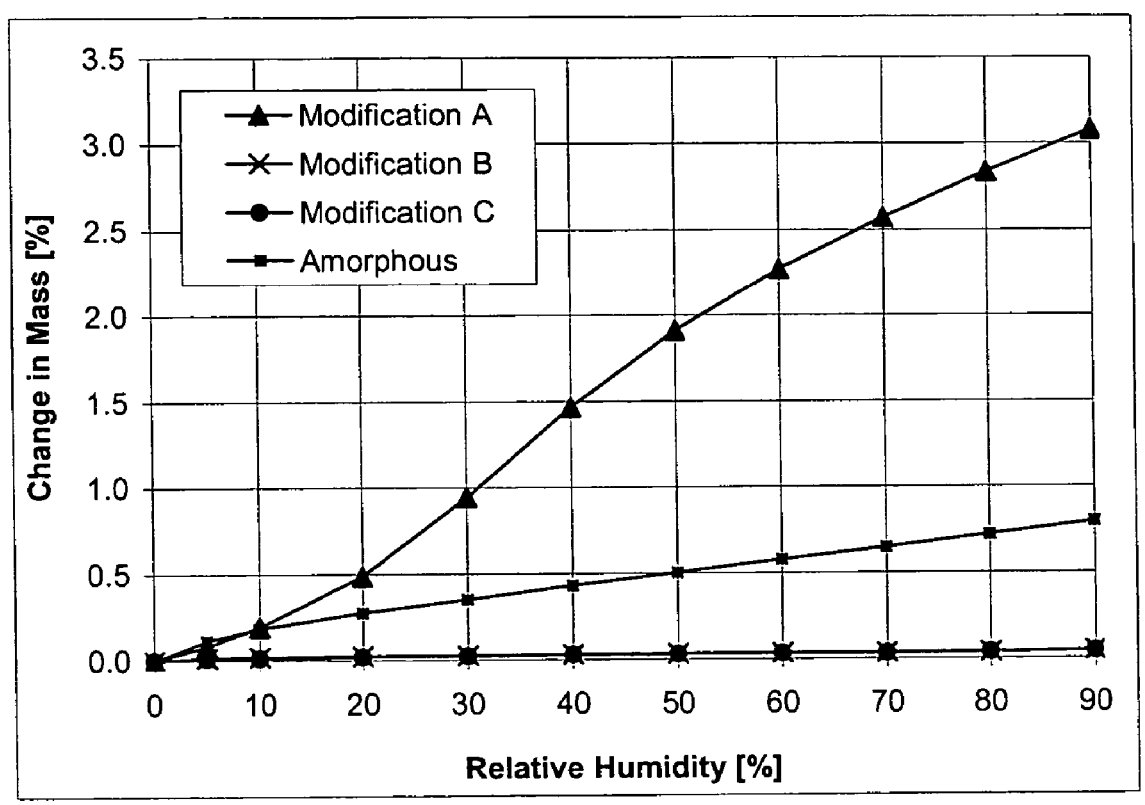
FIG. 5: DVS isotherms of typical lots of different crystal modifications and amorphous state of 2-(3,5-bis-trifluoromethyl-phenyl)-N-[6-(1,1-dioxo-1λ⁶-thiomorpholin-4-yl)-4-(4-fluoro-2-methyl-phenyl)-pyridin-3-yl]-N-methyl-isobutyramide

As shown in FIG. 5, the crystal modifications B and C show very similar DVS behavior (reversible uptake of <0.1%-w/w of water from 0 to 90% RH) which is different from amorphous material (reversible uptake of 0.8%-w/w of water from 0 to 90% RH) and crystal modification A (reversible uptake of 3.1%-w/w of water from 0 to 90% RH).

The present invention also provides pharmaceutical compositions containing modification A of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide, or a pharmaceutically acceptable salt of this compound, and a pharmaceutically acceptable carrier. These pharmaceutical compositions can be in the form of tablets, coated tablets, dragées, hard and soft gelatine capsules, solutions, emulsions or suspensions. The invention also provides a process for the production of such compositions, which comprises bringing modification A into a galenical administration form together with one or more therapeutically inert carriers.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salts" of a compound means salts that are pharmaceutically acceptable, which are generally safe, non-toxic, and neither biologically nor otherwise undesirable, and that possess the desired pharmacological activity of the parent compound. These salts are derived from an inorganic or organic acid or base.

Such salts include:

(i) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluene-sulfonic acid, trimethylacetic acid, 2.2,2-trifluoroacetic acid, and the like; or (ii) salts formed when an acidic proton present in the parent compound either is replaced by a metal ion, e.g., an alkali metal ion, an alkaline earth ion, or an aluminum ion; or co-ordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

Pharmaceutical compositions of the invention, in addition to modification A or its pharmaceutically acceptable salt, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the solutions include, for example, water, polyols, sucrose, invert sugar, glucose, and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention, modification A as well as pharmaceutically acceptable salts of modification A are useful in the control or prevention of illnesses based on the NK1 receptor. Such illnesses include migraine, rheumatoid arthritis, asthma, bronchial hyperreactivity, inflammatory bowel disease. The invention also provides for the treatment of illnesses based on the NK1 receptor, such as Parkinson's disease, anxiety, depression, pain, headache, Alzheimer's disease, multiple sclerosis, oedema, allergic rhinitis, Crohn's disease, ocular injury, ocular inflammatory diseases, psychosis, motion sickness, induced vomiting, emesis, urinary incontinence, psychoimmunologic or psychosomatic disorders, cancer, withdrawal symptoms of addictive drugs from opiates or nicotine, traumatic brain injury, and benign prostatic hyperplasia.

The most preferred indications in accordance with the present invention are those, which include disorders of the central nervous system, for example the treatment or prevention of certain depressive disorders.

In one embodiment, the invention provides a method of treating central nervous system disorders which comprises administering to an individual an effective amount of a crystalline modification of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide in modification A or a pharmaceutically acceptable salt thereof. In another embodiment, the invention provides a method of treating depression which comprises administering to an individual an effective amount of a crystalline modification of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide in modification A or a pharmaceutically acceptable salt thereof. In a third embodiment, the invention provides a method of treating a disease selected from the group consisting of migraine, rheumatoid arthritis, asthma, bronchial hyperreactivity, allergic rhinitis, ocular inflammatory diseases, and oedema which comprises administering to an individual an effective amount of a crystalline modification of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide in modification A or a pharmaceutically acceptable salt thereof The invention also provides a method of treating a disease selected from the group consisting of inflammatory-bowel disease, Crohn's disease, induced vomiting, and emesis which comprises administering to an individual an effective amount of a crystalline modification of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide in modification A or a pharmaceutically acceptable salt thereof. The invention additionally provides a method of treating a disease selected from the group consisting of Parkinson's disease, anxiety, depression, Alzheimer's disease, psychoimmunologic or psychosomatic disorders, and psychosis which comprises administering to an individual an effective amount of a crystalline modification of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide in modification A or a pharmaceutically acceptable salt thereof. The invention further provides a method of treating a disease selected from the group consisting of multiple sclerosis, pain, headache, ocular injury, motion sickness, urinary incontinence, cancer, withdrawal symptoms of addictive drugs from opiates or nicotine, traumatic brain injury, and benign prostatic hyperplasia which comprises administering to an individual an effective amount of a crystalline modification of 2-(3,5-bis-trifluoro-methyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide in modification A or a pharmaceutically acceptable salt thereof.

"Therapeutically effective amount" means an amount that is effective to prevent, alleviate or ameliorate symptoms of disease or prolong the survival of the subject being treated.

The dosage at which modification A or its pharmaceutically acceptable salt is administered can vary within wide limits and will, of course, have to be adjusted to the individual requirements in each particular case. In the case of oral administration the dosage for adults can vary from about 0.01 mg to about 1000 mg per day of a compound of modification A or of the corresponding amount of a pharmaceutically acceptable salt thereof. The daily dosage may be administered as single dose or in divided doses and, in addition, the upper limit can also be exceeded when this is found to be indicated.

EXAMPLES

Example 1

Preparation of N-tert-Butyl-6-chloro-4-(4-fluoro-2-methyl-phenyl)-nicotinamide 3.4 g Magnesium (137.5 mmol) was suspended under argon in 12.0 ml tetrahydrofurane and treated under reflux with a solution of 17.6 ml (137,3 mmol) 2-bromo-5-fluorotoluene in 20 ml tetrahydrofurane. After the addition of the first 3 ml of this solution, the mixture was warmed to start the Grignard reaction. The reaction mixture was stirred for 30 minutes under reflux, cooled to 50° C. and added within 10 minutes to a solution of 10.0 g (97%,45 mmol) N-tert-butyl-6-chloronicotinamide in 50 ml tetrahydrofurane (exothermic reaction). The mixture was stirred at 70 ° C. for 2 hours, cooled to room temperature and a solution of 17.4 g (68,6 mmol, 1.5 eq.) iodine in 100 ml tetrahydrofurane was added slowly (exothermic reaction). The resulting suspension was stirred for 1.7 hours at 50° C., treated at room-temperature with 50 ml water, poured onto 150 ml 2 N aqueous sulfuric acid and treated with 150 ml tert-butyl-methyl-ether. After vigorous stirring, the phases were separated and the organic phase was washed with half-saturated aqueous sodium bicarbonate and with half-saturated aqueous sodium chloride. The aqueous phases were extracted with tert-butyl-methyl-ether. The combined organic extracts were dried, concentrated in a rotary evaporator and dried under high vacuum at room temperature to provide 17.3 g of a yellow oil. This oil was dissolved in dichloromethane and filtered through silica gel eluting with hexane and then with dichloromethane. The fractions with the product were collected and concentrated under reduced pressure to a volume of ca. 200 ml to which 400 ml hexane was added. The solution was concentrated in a rotary evaporator to a volume of ca. 150 ml, the suspension obtained was treated with 200 ml hexane and stirred for 2 hours at 4° C. The precipitate was filtered off, washed with cold hexane/ethyl acetate 19/1 (−20° C.) and dried under high vacuum to yield 8.0 g (55%) N-tert-butyl-6-chloro-4-(4-fluoro-2-methyl-phenyl)-nicotinamide as a light beige powder. The mother liquors were concentrated in a rotary evaporator providing 8.5 g of an orange solid, which was purified by chromatography on silica gel eluting with hexane and then with hexane/ethyl acetate 9/1. The fractions with the product were collected, concentrated and dried under high vacuum to yield 3.8 g (25%) N-tert-butyl-6-chloro-4-(4-fluoro-2-methyl-phenyl)-nicotinamide as a light beige powder.

MS (ISP):m/e=321 (M+H$^+$, 36), 273 (M-tBu, 100).

Example 2

Preparation of N-tert-Butyl-4-(4-fluoro-2-methyl-phenyl)-6-thiomorpholin-4-yl-nicotinamide 9.3 g (29.0 mmol) N-tert-Butyl-6-chloro-4-(4-fluoro-2-methyl-phenyl)-nicotinamide was dissolved in 28.0 ml dimethylsulfoxide and 7.0 g (50.7 mmol) potassium carbonate followed by 4.2 ml (43.5 mmol) thiomorpholine was added. The resulting suspension was stirred at 130° C. for 17 hours, cooled to room temperature and partitioned between 120 ml ethyl acetate and 250 ml half-saturated aqueous sodium chloride solution. The phases were separated and the organic phase was washed with half-saturated aqueous sodium chloride. The aqueous phases were extracted with ethyl acetate. The combined organic extracts were dried and concentrated in a rotary evaporator to give 21.4 g of a yellow oil. This oil was heated to 80° C. and 214 ml n-hexane was added dropwise to obtain a refluxing suspension, which was let to cool to room temperature and further stirred at 0° C. for one hour. The precipitate was filtered off, washed with cold n-hexane/ethyl acetate 9:1 and dried in a vacuum oven to yield 10.1 g (90%) N-tert-butyl-4-(4-fluoro-2-methyl-phenyl)-6-thiomorpholin-4-yl-nicotinamide as a light beige powder of m.p.=163.7–168.7° C.

MS (ISP):m/e=388 (M+H$^+$, 100).

Example 3

Preparation of 4-(4-Fluoro-2-methyl-phenyl)-6-thiomorpholin-4-yl-nicotinamide 9.7 g (25 mmol) N-tert-Butyl-4-(4-fluoro-2-methyl-phenyl)-6-thiomorpholin-4-yl-nicotinamide suspended in 48.5 ml toluene was heated to 95° C. and 24.0 g methanesulfonic acid was added dropwise giving an emulsion, which was stirred at 100° C. for two hours. After cooling to room temperature, the phases were separated and the organic phase was washed with deionized water. The combined aqueous phases were cooled to 0° C. and 28% aqueous sodium hydroxide was slowly added to increase the pH to ca. 12.5. The suspension obtained was extracted with dichloromethane. The combined organic extracts were dried and concentrated in a rotary evaporator. 100 ml Propyl acetate was added and the solution was concentrated in a rotary evaporator. A second portion of 100 ml propyl acetate was added and the solution was concentrated to ca. 23 g, forming a suspension to which 8.3 ml n-hexane was added. The suspension was stirred at 0° C. for one hour. The precipitate was filtered off, washed with n-hexane/propyl acetate 9:1 and dried in a vacuum oven to yield 8.0 g (97 %) 4-(4-fluoro-2-methyl-phenyl)-6-thiomorpholin-4-yl-nicotinamide as a light yellow powder of m.p.=198–202° C.

MS (ISP):m/e=332 (M+H$^+$, 100).

Example 4

Preparation of [4-(4-Fluoro-2-methyl-phenyl)-6-thiomorpholin-4-yl-pyridin-3-yl]-carbamic acid methyl ester 10.5 g (31.7 mmol) 4-(4-Fluoro-2-methyl-phenyl)-6-thiomorpholin-4-yl-nicotinamide were added to a solution of 5.8 g (88.9 mmol) potassium hydroxide in 60 ml methanol cooled to 0° C. 40 ml Methanol was further added and 11.5 g (35 mmol) (diacetoxyiodo)benzene was added in one portion (exothermic). After two hours at 0° C., the reaction mixture was allowed to warm to room temperature, diluted with 250 ml deionized water and concentrated in a rotary evaporator. The residue was diluted with 200 ml ethyl acetate, the phases were separated and the aqueous phase was extracted further with ethyl acetate. The organic phases were washed with half-saturated aqueous sodium chloride. The combined organic extracts were dried, concentrated under reduced pressure and dried under high vacuum to yield 14.9 g [4-(4-fluoro-2-methyl-phenyl)-6-thiomorpholin-4-yl-pyridin-3-yl]-carbamic acid methyl ester as a brown sticky oil which was used in the next step without purification.

MS(ISP):m/e=362 (M+H$^+$, 100).

Example 5

Preparation of Methyl-[4-(4-fluoro-2-methyl-phenyl)-6-thiomorpholin-4-yl-pyridin-3-yl]-amine 43.7 ml Red-Al (3.5 M in toluene) was diluted in 25 ml toluene and added dropwise to a solution of 13 g (30.6 mmol) [4-(4-fluoro-2-methyl-phenyl)-6-thiomorpholin-4-yl-pyridin-3-yl]-carbamic acid methyl ester in 55 ml toluene at 10° C. (the addition was exothermic). The yellow solution obtained was stirred for 40 minutes at room temperature and 1.5 hours at 50° C. It was cooled to 0° C. and poured slowly onto a mixture of 150 ml 4 N aqueous sodium hydroxide and 50 ml ice (very exothermic). After 10 minutes stirring, the phases were separated, the aqueous phase was extracted with tert-butyl-methyl-ether and the organic phases were washed with brine. The combined organic extracts were dried and concentrated under reduced pressure to yield 10 g methyl-[4-(4-fluoro-2-methyl-phenyl)-6-thiomorpholin-4-yl-pyridin-3-yl]-amine as a brown oil which was used in the next step without further purification.

MS (ISP):m/e=350 (M+Na$^+$, 17), 318 (M+H$^+$, 100).

Example 6

Preparation of 2-(3,5-Bis-trifluoromethyl-phenyl)-N-methyl-N-[4-(4-fluoro-2-methyl-phenyl)-6-thiomorpholin-4-yl-pyridin-3-yl]-isobutyramide A solution of 8.5 g (26.6 mmol) 2-(3,5-bis-trifluoromethyl-phenyl)-2-methyl-propionyl chloride in 12 ml dichloromethane was added dropwise at room temperature to a solution of 8.0 g (24.2 mmol) methyl-[4-(4-fluoro-2-methyl-phenyl)-6-thiomorpholin-4-yl-pyridin-3-yl]-amine and 4.7 ml (33.9 mmol) triethylamine in 65 ml dichloromethane. The reaction mixture was stirred for 1 hour and poured onto 50 ml 1 N aqueous sodium hydroxide. After extraction the phases were separated, the aqueous phase was extracted with dichloromethane and the organic phases were washed with water. The combined organic extracts were concentrated under reduced pressure and the solvent was exchanged for 150 ml ethanol. The solution was seeded at 40° C. with some crystals, 30 ml water were slowly added and the system was stirred for 1 hour at room temperature and for 1 hour at 0° C. The precipitate was filtered off, washed with cold ethanol (0° C.) and dried under high vacuum to yield 13.0 g (76% over 3 steps) 2-(3,5-bis-trifluoromethyl-phenyl)-N-methyl-N-[4-(4-fluoro-2-methyl-phenyl)-6-thiomorpholin-4-yl-pyridin-3-yl]-isobutyramide as an off-white powder of m.p.=168–170° C. MS (ISP):m/e=600 (M+H$^+$, 100), 279 (31).

Example 7

Preparation of 2-(3,5-Bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide 5.0 g (8.3 mmol) 2-(3,5-Bis-trifluoromethyl-phenyl)-N-methyl-N-[4-(4-fluoro-2-methyl-phenyl)-6-thiomorpholin-4-yl-pyridin-3-yl]-isobutyramide was suspended in 50 ml methanol and treated at room temperature with 6.4 g (10.4 mmol) oxone™. The suspension was stirred for 16 hours at room temperature, cooled to 0° C. and 3.4 ml (16.7 mmol) sodium hydrogen sulfite solution was added dropwise. The stirring was pursued for 30 minutes at room temperature and the pH adjusted to ca. 8.5 with saturated aqueous sodium carbonate. The methanol was evaporated under reduced pressure and the residue was extracted with dichloromethane. The organic phase was washed with half-saturated aqueous sodium chloride. The solvent was exchanged under reduced pressure in a rotary evaporator with 60 ml isopropanol and the volume reduced to ca. 40 ml. The solution was cooled to room temperature under stirring within 2 hours and stirred further for 1 hour. The precipitate formed was filtered off, washed with 5 ml isopropanol and dried under high vacuum to yield 4.4 g (83.5%) 2-(3,5-bis-trifluoromethyl-phenyl)-N-[6-(1,1-dioxothiomorpholin-4-yl)-4-(4-fluoro-2-methyl-phenyl)-pyridin-3-yl]-N-methyl-isobutyramide as a white powder of m.p.=135–138° C.

$^1$H-NMR (CDCl$_3$, 300 MHz): 8.02 [s, 1H], 7.78 [s, 1H], 7.65 [s, 2H], 6.97 [s$_{br}$, 3H], 6.58 [s, 1H, 8 H$_{arom}$]; 4.17 [m, 4H, CH$_2$–N–CH$_2$]; 3.07 [t, 4H, CH$_2$–SO$_2$–CH$_2$], 260—2.12 [m, 6H], 1.52—1.20 [m, 6H, 4 CH$_3$]. MS (ISP): m/e=673 (M+CH$_3$CN+H$^+$, 36), 650 (29), 649 (M+NH$_4^+$, 94), 633 (M+H$^+$, 100), 279 (73).

The different modifications A, B and C and the amorphous form may be prepared from 2-(3,5-bis-trifluoromethyl-phenyl)-N-[6-(1,1-dioxothiomorpholin-4-yl)-4-(4-fluoro-2-methyl-phenyl)-pyridin-3-yl]-N-methyl-isobutyramide as follows:

Example 8

Preparation of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide (Modification A)

10.0 g of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide were dissolved in 78.5 g of 2-propanol at reflux conditions. After polishing filtration, the solution was stirred and linearly cooled from 75° C. to 10° C. over a period of 6 h. The slurry was stirred for additional 4 h at 10° C., before the crystals were harvested by filtration. The colorless solid was rinsed with 8.0 g of cold 2-propanol (10° C.) and dried in vacuum (5 mbar) at 80° C. for 12 h, yielding 9.1 g (91 %) of 2-(3,5-bis-trifluoromethyl-phenyl)-N-[6-(1,1-dioxothiomorpholin-4-yl)-4-(4-fluoro-2-methyl-phenyl)-pyridin-3 -yl]-N-methyl-isobutyramide in crystal modification A.

Crystal modification A can also be prepared using 1-propanol instead of 2-propanol, but otherwise following the protocol above. Alternatively, crystal modification A is obtained from any other modification known by digestion with 1-propanol, 2-propanol or a mixture of ethanol/dichloromethane/water.

Example 9

Preparation of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide (Modification B)

4.0 g of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide were dissolved in 19.8 g of ethanol at 75° C. After polishing filtration, the solution was stirred and linearly cooled from 75° C. to 20° C. over a period of 48 h. After filtration, the colorless solid was rinsed with 4.75 g of ethanol and dried in vacuum (5 mbar) at 60° C. for 6 h, yielding 3.4 g (84%) of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide in crystal modification B.

Alternatively, crystal modification B is obtained by digestion of any other modification known with acetonitrile, cyclohexane, ethanol, n-hexane, methanol, methyl t-butyl ether or water.

Example 10

Preparation of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide (Modification C)

3.0 g of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide in modification A were incubated at 120° C. in vacuum (5 mbar) for 3 days. After cooling to ambient temperature 2.9 g (97%) slightly beige crystals of 2-(3,5-bis-trifluoromethyl-phenyl)-N-[6-

(1,1-dioxo-1λ$^6$-thiomorpholin-4-yl)-4-(4-fluoro-2-methyl-phenyl)-pyridin-3-yl]-N-methyl-isobutyramide in crystal modification C were obtained.

Example 11

Preparation of 2-(3,5-bis-trifluoromethyl-phenyl)-N-[6-(1,1-dioxo-1λ$^6$-thiomorpholin-4-yl)-4-(4-fluoro-2-methyl-phenyl)-pyridin-3-yl]-N-methyl-isobutyramide (Amorphous)

A solution of 40 g 2-(3,5-bis-trifluoromethyl-phenyl)-N-[6-(1,1-dioxo-1λ$^6$-thiomorpholin-4-yl)-4-(4-fluoro-2-methyl-phenyl)-pyridin-3-yl]-N-methyl-isobutyramide in 400 g dichloromethane was rapidly vacuum concentrated at room temperature using a rotary evaporator. The resulting slightly beige foam was further dried in vacuum (5 mbar) at ambient temperature for 12 h, yielding 39 g (98%) 2-(3,5-bis-trifluoromethyl-phenyl)-N-[6-(1,1-dioxo-1λ$^6$-thiomorpholin-4-yl)-4-(4-fluoro-2-methyl-phenyl)-pyridin-3-yl]-N-methyl-isobutyramide in amorphous state.

Alternatively, amorphous material is obtained by fast evaporation of solutions in dioxane, ethyl acetate, isopropyl acetate, methyl ethyl ketone or tetrahydrofurane.

The crystal modifications and the amorphous material may clearly be distinguished by their physicochemical data as described below:

Physicochemical Characterization of the Different Crystal Modifications:

Example 12

XRPD (X-Ray Powder Diffraction)

XRPD patterns were recorded on a Bruker D8 diffractometer in reflexion mode. Measuring time 1 second per step, step size 0.02 degree and copper K-Alpha 1 radiation (1.54056 Å) at 40 KV, 50 mA. The samples were measured between 2 and 42 2Theta (2θ). The crystal modifications A, B and C and the amorphous material can clearly be distinguished by their X-ray powder diffraction patterns as shown in FIG. 1.

The X-ray diffraction pattern for modification A shows peaks at 4.5, 6.4, 7.5, 7.7, 8.0, 8.2, 10.0, 10.2, 10.9, 11.1, 12.9, 13.4, 14.0, 14.5, 15.1, 15.6, 16.2, 16.5, 17.3, 17.5, 18.0, 18.9, 19.3, 19.5, 19.9, 20.1, 20.6, 21.0, 21.4, 22.7, 23.1 and 23.6 2Theta (2θ).

Example 13

Infrared Spectroscopy (IR)

The IR-spectra of the samples were recorded as film of a Nujol suspension consisting of approximately 15 mg of sample and approximately 15 mg of Nujol between two sodium chloride plates, with an FT-IR spectrometer in transmittance. The Spectrometer was a Nicolet 20SXB or equivalent (resolution 2 cm$^{-1}$, 32 or more coadded scans, MCT detector).

The crystal modifications A, B, C and amorphous state could also clearly be distinguished by solid state IR as shown in FIG. 2. The IR spectra of modification A also is shown in FIG. 3.

Example 14

Differential Scanning Calorimetry (DSC)

The DSC-thermograms were recorded using a Mettler-Toledo differential scanning calorimeter (DCS-820, DSC-821, respectively, with FRS05 sensors, calibrated using Biphenyl, Benzoic acid, Indium and Zinc).

For the measurements of 2-(3,5-bis-trifluoromethyl-phenyl)-N-[6-(1,1-dioxo-1λ$^6$-thiomorpholin-4-yl)-4-(4-fluoro-2-methyl-phenyl)-pyridin-3-yl]-N-methyl-isobutyramide approximately 2 mg to 6 mg of the sample were placed in aluminum pans, accurately weighed and hermetically closed with perforation lids. Prior to measurement, the lids were automatically pierced resulting in approximately 1.5 mm pin holes. The samples were then heated under a flow of nitrogen of about 100 mL/min using a heating rate of 5 K/min to a maximum temperature of 180° C.

The crystal modifications A, B and C can be distinguished by their melting behavior as depicted in FIG. 4.

Amorphous material exhibits a glass transition. Thermoanalytical properties of typical lots of modification A, B, C and of the amorphous form of 2-(3,5-bis-trifluoromethyl-phenyl)-N-[6-(1,1-dioxo-1λ$^6$-thiomorpholin-4-yl)-4-(4-fluoro-2-methyl-phenyl)-pyridin-3-yl]-N-methyl-isobutyramide.

TABLE 1

| Crystall Modification | Modification A | Modification B | Modification C | Amorphous state |
|---|---|---|---|---|
| Melting Temperature (extrapolated peak [° C.] from DCS) | 137.2 | 166.7 | 166.0 | — |
| Glass Transition Temperature (midpoint of 2$^{nd}$ heating) [° C.] | — | — | — | 81.5 |
| Enthalpy of fusion [J/g] | 43.0 | 60.8 | 46.4 | — |
| Weight loss (TGA) [%-w/w] | 1.3 | <0.1 | <0.1 | 0.21 |

The melting temperatures of single lots of modification A may vary within 128.3–148.5° C., of modification B within 161.8–171.3 and of modification C within 164.8–169.7, depending on their content of residual solvent.

Example 15

Dynamic Vapor Sorption (DVS)

As shown in FIG. 5, the crystal modifications B and C show very similar DVS behavior (reversible uptake of <0.1%-w/w of water from 0 to 90% RH) which is different from amorphous material (reversible uptake of 0.8%-w/w of water from 0 to 90% RH) and crystal modification A (reversible uptake of 3.1%-w/w of water from 0 to 90% RH).

The different physicochemical properties of modifications A, B, and C and the amorphous form lead to different pharmacological properties, especially to different pharmacokinetic parameter as shown below:

Example 16

Crystalline Material, Forms A, B, and C:

Four male beagle dogs (age 5 to 6 years, body weight 11 to 14 kg) received single oral doses of 2 mg/kg of 2-(3,5-bis-trifluoromethyl-phenyl)-N-[6-(1,1-dioxo-1λ$^6$-thiomorpholin-4-yl)-4-(4-fluoro-2-methyl-phenyl)-pyridin-3-yl]-N-methyl-isobutyramide form A and form B (cross-over study design). The formulation was a granulate of the finely milled compound with 20% sodium dodecyl sulfate (SDS) in gelatine capsules.

In addition, four male beagle dogs (age 4 to 7 years, body weight 11 to 14 kg) received a single oral dose of 2 mg/kg of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide form C as finely milled compound with 10% SDS in gelatine capsules. The dogs received 200 g commercial dog chow (Pal®, approx. 7% fat content) about 30 minutes before administration of the compound.

Amorphous Material:

Two dogs (age 8 years, body weight 12 to 14 kg) received 5 mg/kg of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide as amorphous material orally by gavage as microsuspension. The dogs were fed before and during the experiment.

Plasma samples were drawn at several time points. 2-(3,5-bis-Trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide plasma concentrations were determined using a selective LC-MS method with a quantification limit of 10 ng/mL. Pharmacokinetic parameters (e.g. AUC, Cmax) were estimated by non-compartmental analysis using WinNonlin 3.1®.

Results

Mean $C_{max}$ and oral bioavailability were 1.7- and 1.9-fold higher after administration of form A as compared to form B. Looking at individual animals, 3 out of 4 animals showed a significant difference in 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide plasma exposure after administration of form A (2.1- to 3.8-fold difference in terms of oral bioavailability between form A and form B).

Form C led to approximately the same mean $C_{max}$ and AUC(0–24 h) values as form A.

After administration of the amorphous material (as microsuspension), mean exposure to 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide was higher than after administration of the crystalline material in gelatine capsules (approximately 1.3- to 2-fold).

Table 2

Individual and mean pharmacokinetic parameters of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide after single oral administration of 2 mg/kg Form A and Form B to fed male beagle dogs (cross-over study).

| Dog | $C_{max}$ [ng/mL] Form A | $C_{max}$ [ng/mL] Form B | C(24 h) [ng/mL] Form A | C(24 h) [ng/mL] Form B | AUC(0–24 h) [h·ng/mL] Form A | AUC(0–24 h) [h·ng/mL] Form B | F [%] Form A | F [%] Form B |
|---|---|---|---|---|---|---|---|---|
| Charly | 391 | 122 | 47.6 | 17.7 | 3720 | 949 | 24.5 | 6.3 |
| Lars | 744 | 631 | 28.2 | 51.7 | 2520 | 3880 | 18.2 | 21 |
| Lupo | 424 | 216 | 40.3 | 23.2 | 2490 | 1130 | 16.2 | 6.8 |
| Mickey | 496 | 251 | 29.8 | 21.4 | 2900 | 1330 | 17.4 | 8.2 |
| Mean | 514 | 305 | 36.5 | 28.5 | 2910 | 1822 | 19.1 | 11.0 |
| SD % | 31 | 73 | 25 | 55 | 20 | 76 | 19 | 66 |

Table 3

Mean pharmacokinetic parameters of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide after single oral administration of 2 mg/kg Form C (n=4).

| | $C_{max}$ [ng/mL] | C(24 h) [ng/mL] | AUC(0–24 h) [h·ng/mL] | F [%] |
|---|---|---|---|---|
| Mean | 510 | 29.2 | 2660 | 13.3 |
| SD % | 29 | 24 | 28 | 30 |

Table 4

Mean pharmacokinetic parameters of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide after single oral administration of 5 mg/kg amorphous material (n=2, compound administered by gavage as microsuspension).

| | $C_{max}$ [ng/mL] | C(24 h) [ng/mL] | AUC(0–24 h) [h-ng/mL] | F [%] |
|---|---|---|---|---|
| Mean | 3050 | 123 | 10400 | 1 24.5 |

Table 5

Mean pharmacokinetic parameters of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide after single oral administration of 2 mg/kg form A, B, C, and amorphous material to fed male beagle dogs.

| Form A | Form B | Form C | Amorphous* | Form A | Form B | Form C | Amorphous* |
|---|---|---|---|---|---|---|---|
| $C_{max}$ [ng/mL] | | | | C(24 h) [ng/mL] | | | |
| 514 | 305 | 510 | 1220 | 36.5 | 28.5 | 29.2 | 49.2 |
| AUC(0–24 h) [h·ng/mL] | | | | F [%] | | | |
| 2910 | 1822 | 2660 | 4160 | 19.1 | 11.0 | 13.3 | 24.5 |

*values normalized to 2 mg/kg

Figure 6:
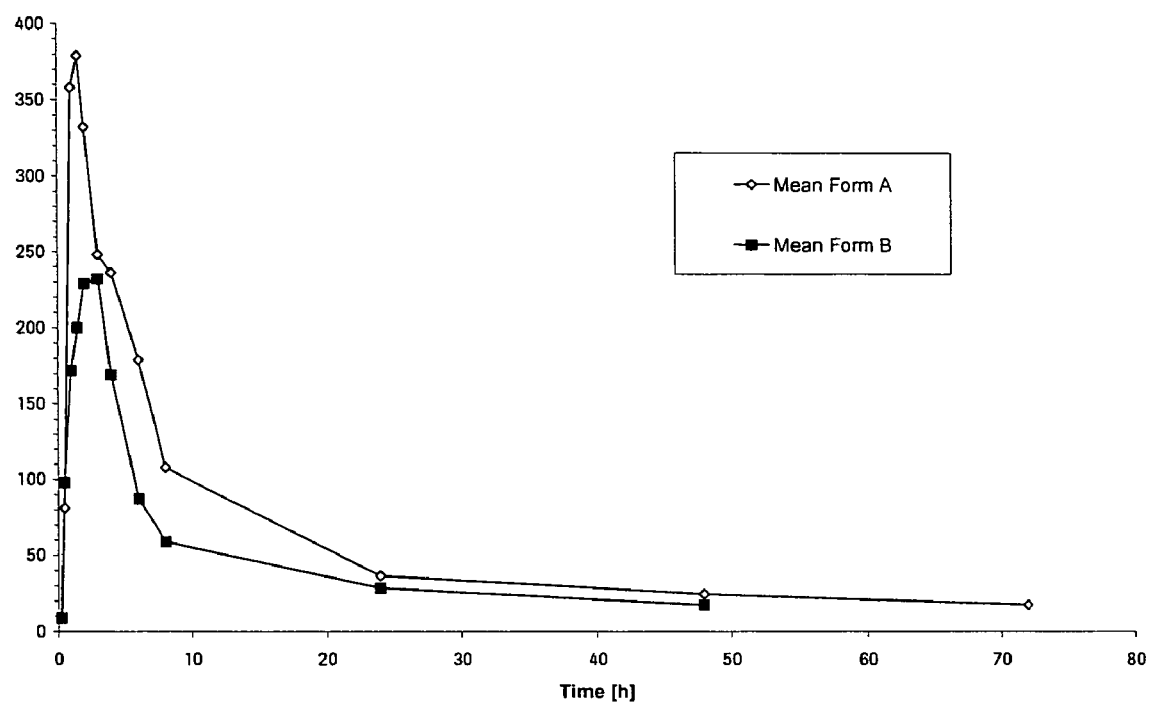
FIG. 6: Mean of 2-(3,5-bis-trifluoromethyl-phenyl)-N-[6-(1,1-dioxo-1λ⁶-thio-morpholin-4-yl)-4-(4-fluoro-2-methyl-phenyl)-pyridin-3-yl]-N-methyl-isobutyramide plasma concentrations (n=4) after single oral administration of 2 mg/kg form A and form B to fed male beagle dogs (cross-over study).
Figure 7:
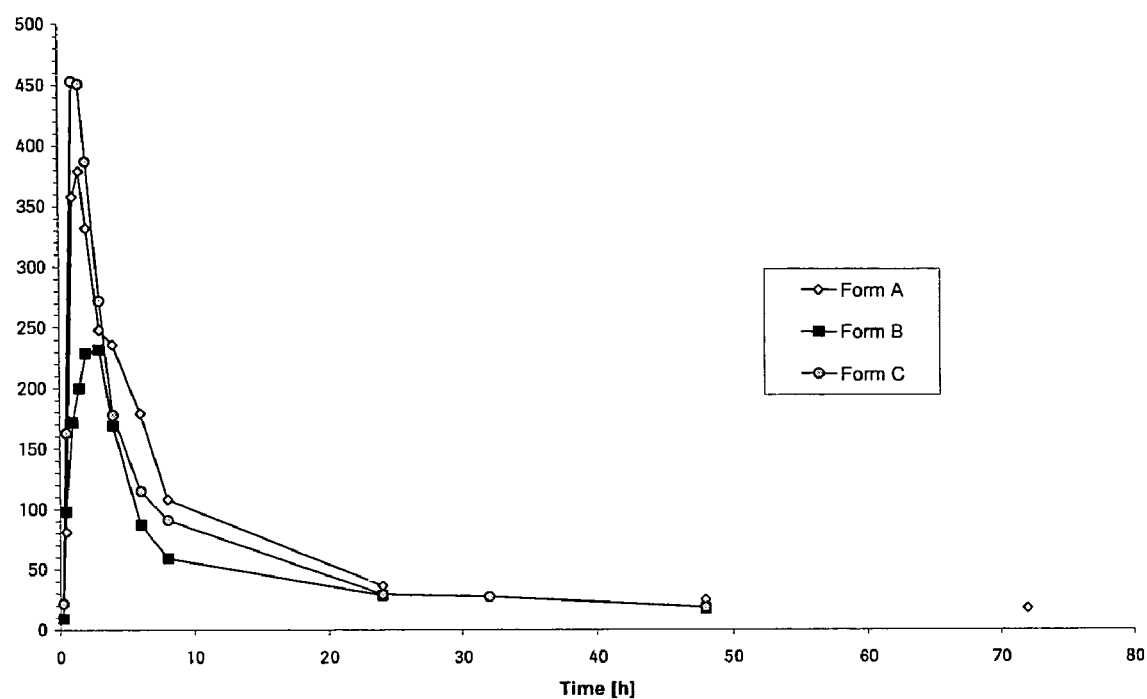
FIG. 7: Mean of 2-(3,5-bis-trifluoromethyl-phenyl)-N-[6-(1,1-dioxo-1$\lambda^6$-thio-morpholin-4-yl)-4-(4-fluoro-2-methyl-phenyl)-pyridin-3-yl]-N-methyl-isobutyramide plasma concentrations (n=4) after single oral administration of 2 mg/kg form A, B, and C to fed male beagle dogs.
Figure 8:
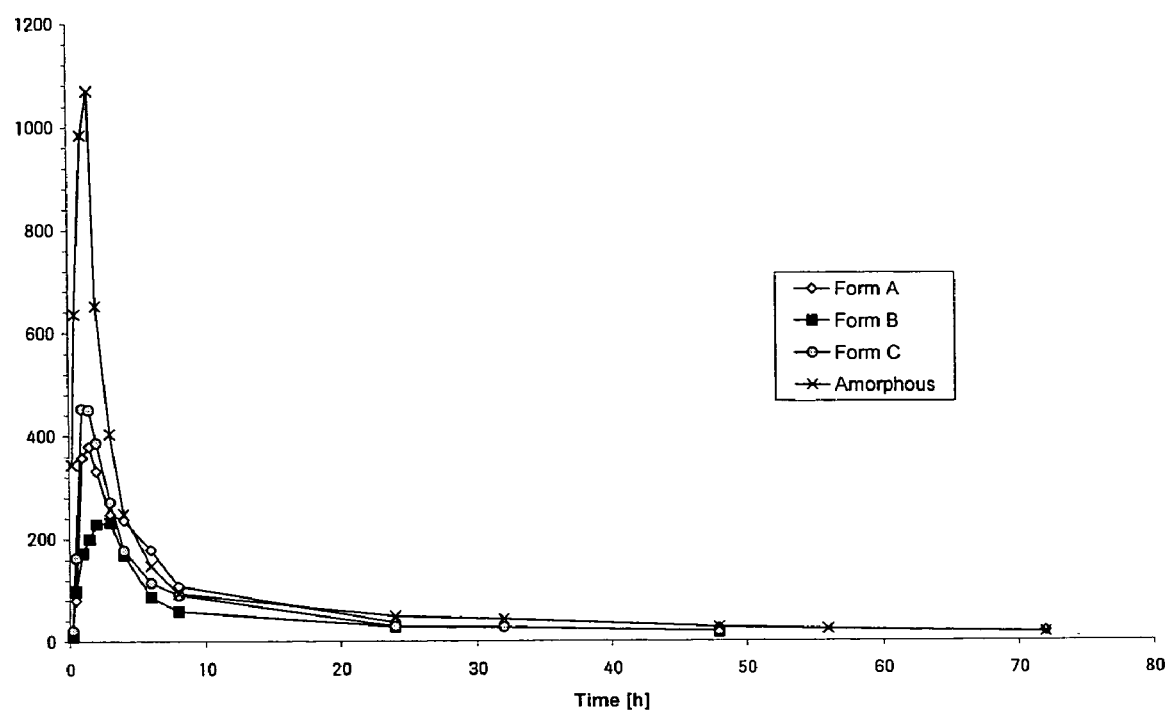
FIG. 8: Mean of 2-(3,5-bis-trifluoromethyl-phenyl)-N-[6-(1,1-dioxo-1$\lambda^6$-thio-morpholin-4-yl)-4-(4-fluoro-2-methyl-phenyl)-pyridin-3-yl]-N-methyl-isobutyramide plasma concentrations (n=4 for form A, B, and C; n=2 for amorphous) after single oral administration of 2 mg/kg fed male beagle dogs (for amorphous 5 mg/kg, curve normalized to 2 mg/kg).

FIG. 6 shows the mean plasma concentrations (n=4) of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide after single oral administration of 2 mg/kg of form A and form B to fed male beagle dogs (cross-over study). FIG. 7 shows the mean plasma concentrations (n=4) of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide after single oral administration of 2 mg/kg of form A, B, or C to fed male beagle dogs. FIG. 8 shows the mean plasma concentrations of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl isobutyramide after single oral administration of 2 mg/kg of forms A, B, and C (n=4) and after a single oral administration of 5 mg/kg (curve normalized for 2 mg/kg) of the amorphous form (n=2).

In summary it can be said, that as expected, amorphous material administered as a microsuspension led to the highest 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide exposure after oral administration of the compound to beagle dogs. Form A demonstrated the highest bioavailability among the three crystalline polymorphs A, B, and C after administration of the compound as powder in gelatine capsules (containing sodium dodecyl sulfate).

For oral administration the crystalline modification A is preferred.

Example A

Tablet Formulation (Wet Granulation)

| Item | Ingredients | 5 mg | 25 mg | 100 mg | 500 mg |
|---|---|---|---|---|---|
| 1. | modification A | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Example B

Capsule Formulation

| Item | Ingredients | 5 mg | 25 mg | 100 mg | 500 mg |
|---|---|---|---|---|---|
| 1. | modification A | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The invention claimed is:

1. A crystalline form of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide characterized by the following X-ray diffraction pattern obtained with a Cu$_{K\alpha}$ radiation at 2θ (2Theta)=4.5, 6.4, 7.5, 7.7, 8.0, 8.2, 10.0, 10.2, 10.9, 11.1, 12.9, 13.4, 14.0, 14.5, 15.1, 15.6, 16.2, 16.5, 17.3, 17.5, 18.0, 18.9, 19.3, 19.5, 19.9, 20.1, 20.6, 21.0, 21.4, 22.7, 23.1 and 23.6 and an infrared spectrum having sharp bands at 2925, 2854, 1637, 1604, 1484, 1395, 1375, 1285, 1230, 1172, 1125, 1082, 999, 943, 893, 868, 860, 782, 705, 684 cm$^{-1}$, and wherein the extrapolated melting point (DSC) is 137.2° C. or a pharmaceutically acceptable salt thereof.

2. A pharmaceutically acceptable composition comprising the crystalline form of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide characterized by the following X-ray diffraction pattern obtained with a CU$_{K\alpha}$ radiation at 2θ(2Theta)=4.5, 6.4, 7.5, 7.7, 8.0, 8.2, 10.0, 10.2, 10.9, 11.1, 12.9, 13.4, 14.0, 14.5, 15.1, 15.6, 16.2, 16.5, 17.3, 17.5, 18.0, 18.9, 19.3, 19.5, 19.9, 20.1, 20.6, 21.0, 21.4, 22.7, 23.1 and 23.6 and an infrared spectrum having sharp bands at 2925, 2854, 1637, 1604, 1484, 1395, 1375, 1285, 1230, 1172, 1125, 1082, 999, 943, 893, 868, 860, 782, 705, 684 cm$^{-1}$, and wherein the extrapolated melting point (DSC) is 137.2°0C. or a pharmaceutically acceptable salt thereof-and a pharmaceutically acceptable carrier.

3. A pharmaceutically acceptable composition according to claim 2, wherein the crystalline form of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide is administered as powder in gelatine capsules.

4. A process for the manufacture of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide as defined in claim 1 comprising
(a) dissolving 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide in 2-propanol under reflux conditions;
(b) subjecting the solution in (a) to polishing filtration;
(c) cooling the solution while stirring over a period of about 6 hours to a temperature of about 10° C.;
(d) stirring the slurry at about 10° C. until crystals form; and
(e) harvesting the crystals by filtration.

5. A process for the manufacture of 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide as defined in claim 4 comprising
  (a) dissolving 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide in 1-propanol under reflux conditions;
  (b) subjecting the solution in (a) to polishing filtration;
  (c) cooling the solution while stirring over a period of about 6 hours to a temperature of about 10° C;.
  (d) stirring the slurry at about 10° C. until crystals form; and
  (e) harvesting the crystals by filtration.

6. The process of claim 4 wherein the 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide employed in step (a) is prepared by the process comprising
  (a) reacting magnesium, 2-bromo-5-fluorotoluene, and N-tert-butyl-6-chloronicotinamide under reflux to produce N-tert-butyl-6-chloro-4-(4-fluoro-2-methyl-phenyl)-nicotinamide;
  (b) isolating the N-tert-butyl-6-chloro-4-(4-fluoro-2-methyl-phenyl)-nicotinamide;
  (c) reacting N-tert-butyl-6-chloro-4-(4-fluoro-2-methyl-phenyl)-nicotinamide with potassium carbonate and thiomorpholine to produce N-tert-butyl-4-(4-fluoro-2-methyl-phenyl)-6-thiomorpholin-4-yl-nicotinamide;
  (d) isolating the N-tert-butyl-4-(4-fluoro-2-methyl-phenyl)-6-thiomorpholin-4-yl-nicotinamide;
  (e) adding methanesulfonic acid dropwise to the N-tert-butyl-4-(4-fluoro-2-methyl-phenyl)-6-thiomorpholin-4-yl-nicotinamide to produce an emulsion to produce 4-(4-fluoro-2-methyl-phenyl)-6-thiomorpholin-4-yl-nicotinamide;
  (f) isolating the 4-(4-fluoro-2-methyl-phenyl)-6-thiomorpholin-4-yl-nicotinamide;
  (g) reacting 4-(4-fluoro-2-methyl-phenyl)-6-thiomorpholin-4-yl-nicotinamide and potassium hydroxide, methanol, and (diacetoxyiodo)benzene to produce [4-(4-fluoro-2-methyl-phenyl)-6-thiomorpholin-4-yl-pyridin-3-yl]-carbamic methyl ester;
  (h) adding a solution of Red-Al dropwise to the [4-(4-fluoro-2-methyl-phenyl)-6-thiomorpholin-4-yl-pyridin-3-yl]-carbamic methyl ester to produce methyl-[4-(4-fluoro-2-methyl-phenyl)-6-thiomorpholin-4-yl-pyridin-3-yl]-amine;
  (i) adding a solution of 2-(3,5-bis-trifluoromethyl-phenyl)-2-methyl-propionyl chloride dropwise into a solution of the methyl-[4-(4-fluoro-2-methyl-phenyl)-6-thiomorpholin-4-yl-pyridin-3-yl]-amine to produce 2-(3,5-bis-trifluoromethyl-phenyl)-N-methyl-[4-(4-fluoro-2-methyl-phenyl)-6-thiomorpholin-4-yl-pyridin-3-yl]-isobutyramide; and
  (j) treating the 2-(3,5-bis-trifluoromethyl-phenyl)-N-methyl-[4-(4-fluoro-2-methyl-phenyl)-6-thiomorpholin-4-yl-pyridin-3-yl]-isobutyramide with oxone at room temperature followed by cooling to about 0° C. followed by the dropwise addition of sodium hydrogen sulfite solution to produce 2-(3,5-bis-trifluoromethyl-phenyl)-N-methyl-[6-(1,1-dioxo-1$\lambda^6$-thiomorpholin-4-yl)-4-(4-fluoro-2-methyl-phenyl)-pyridin-3-yl]-N-methyl-isobutyramide.

* * * * *